United States Patent [19]
Takao et al.

[11] 3,941,673
[45] Mar. 2, 1976

[54] OXYGEN SENSOR DEVOID OF CATALYTIC OXIDATION ACTIVITY

[75] Inventors: Hiroshi Takao, Kamakura; Kinmochi Togawa, Zushi; Kazuo Matoba, Yokohama; Yoshitaka Hata, Fujisawa, all of Japan

[73] Assignee: Nissan Motor Co., Ltd., Japan

[22] Filed: Aug. 5, 1974

[21] Appl. No.: 494,890

[30] Foreign Application Priority Data
Aug. 29, 1973  Japan.............................. 48-96219

[52] U.S. Cl. ............ 204/195 S; 75/172 R; 427/125
[51] Int. Cl.² ................. G01N 27/30; G01N 27/46
[58] Field of Search ........ 204/195 S, 1 T; 136/86 F; 324/29

[56] References Cited
UNITED STATES PATENTS

| | | | |
|---|---|---|---|
| 3,216,911 | 11/1965 | Kronenberg | 204/1 T |
| 3,481,855 | 12/1969 | Kolodney et al. | 204/195 S |
| 3,597,345 | 8/1971 | Hickham et al. | 204/195 S |
| 3,768,259 | 10/1973 | Carnahan et al. | 204/195 S X |
| 3,791,953 | 2/1974 | Minushkin et al. | 204/195 S |
| 3,819,500 | 6/1974 | VanEsdonk et al. | 204/195 S |

*Primary Examiner*—G. L. Kaplan
*Attorney, Agent, or Firm*—Robert E. Burns; Emmanuel J. Lobato; Bruce L. Adams

[57] ABSTRACT

An electrode of an oxygen sensor of the concentration cell type is made of a material such as Au or a Pt/Pb/S mixture, which material is devoid of catalytic oxidizing effect on CO and HC in an engine exhaust gas, so that the EMF characteristics depend on actual $O_2$ concentrations.

3 Claims, 5 Drawing Figures

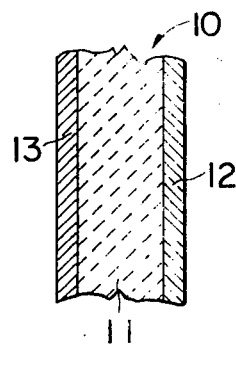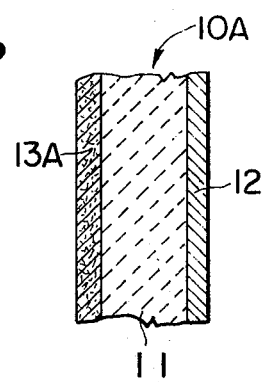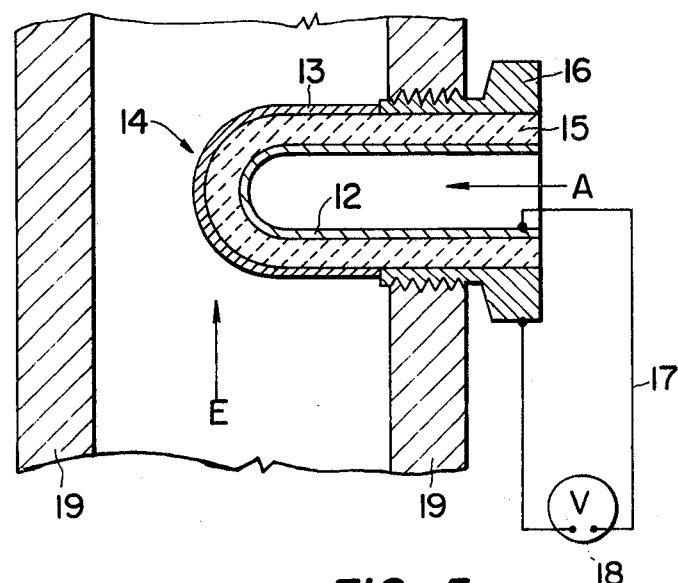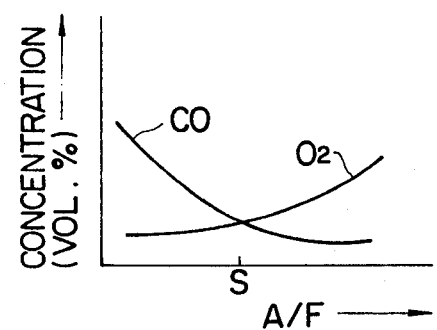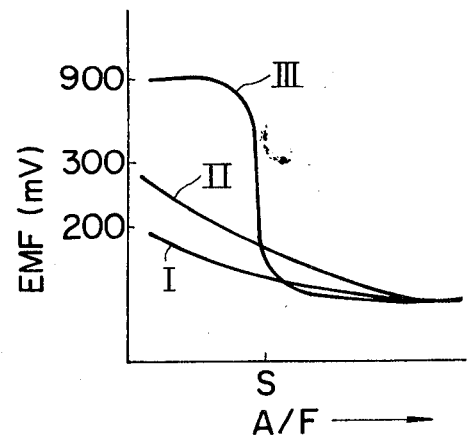

OXYGEN SENSOR DEVOID OF CATALYTIC OXIDATION ACTIVITY

The present invention generally relates to a concentration cell of the solid oxygen-ion electrolyte type, and more particularly to an oxygen sensor essentially consisting of such a cell, wherein catalytic oxidizing effect on a gas being subjected to oxygen concentration measurement is absent.

An oxygen concentration cell can be used to measure oxygen concentration in a mixed gas because the magnitude of the electromotive force (EMF) between the two electrodes of such a cell is dependent on the oxygen concentration difference between the atmospheres surrounding the respective electrodes. When one of the electrodes is allowed to communicate with a reference gas such as air, variation of oxygen concentration in a sample gas can be detected continuously. A solid electrolyte such as an oxide of a certain kind of tetravalent element in which oxygen ion functions as electron carrier is commonly employed to make a cell available as a practical oxygen sensor. This type of oxygen sensor thus far provided consists of a layer of stabilized zirconia $ZrO_2$ as the electrolyte, which is a solid solution of $ZrO_2$ and a stabilizer such as calcia CaO, and a pair of platinum electrodes deposited on the surfaces of the electrolyte layer.

It is known to employ such an oxygen sensor in a control system for automatically controlling the air to fuel ratio (A/F) of a combustible mixture fed to an engine, especially an automobile engine, in order to achieve top engine efficiency and/or to produce an innoxious or clean exhaust gas. The oxygen sensor is usually disposed in the exhaust system of the engine to measure oxygen concentration in the exhaust gas using air as a reference gas and thereby to determine actual A/F values of an air-fuel mixture being supplied to the engine.

It is, however, a problem that the magnitude of the EMF developed in the sensor is not in accordance with the Nernst's equation $$EMF = \frac{RT}{4F} \ln \frac{(PO_2)_1}{(PO_2)_2}$$

where R is the gas constant, T is the absolute temperature, F is the Faraday constant, $(PO_2)$ is the partial pressure of oxygen, and the subscripts 1 and 2 refer to the reference air and exhaust gas, respectively.

In actual observations, the EMF of such a sensor remains at a nearly constant value when the A/F is lower than the stoichiometric ratio and shifts rather abruptly to another value considerably different from the former if the A/F is raised above the stoichiometric ratio, while the actual oxygen concentration in the exhaust gas shows a progressive increase as the A/F increases.

The reason for the discrepancy between the theoretical and actual EMF values is considered to be attributable to the catalytic action of the platinum electrode communicating with the exhaust gas. Since platinum is a catalytic substance for oxidation reactions, carbon monoxide and unburned hydrocarbons in the exhaust gas react with the co-existing oxygen on the surface of the electrode until equilibrium is almost established. As the result of the oxygen consumption, the partial pressure of oxygen on the electrolyte becomes lower than the theoretical values corresponding to non-equilibrium states, especially by a large magnitude when the concentrations of oxygen and oxidizable substances in the exhaust gas are low and high, respectively, that is, when the A/F is lower than the stoichiometric value.

Accordingly, a conventional oxygen sensor of the above described type may be of use in a control system for regulating the A/F intermittently or in an on-and-off mode bordering the stoichiometric ratio, but is of little use in measuring oxygen concentration in an exhaust gas quantitatively thereby to enable a continuous and minute control of the A/F.

It is therefore an object of the present invention to provide an oxygen sensor which has no catalytic action with respect to oxidation reactions in an exhaust gas and developes an EMF in accordance with the Nernst's equation.

According to the invention, in an oxygen sensor having a layer of a solid oxygen-ion electrolyte, a first electrode formed on a surface of the layer to communicate with a reference gas and a second electrode formed on the opposite surface of the layer to communicate with a gas subject to measurement, the improvement comprises the second electrode being made of an electrically conductive material being devoid of catalytic action with respect to oxidation of carbon monoxide and hydrocarbons.

The material of the second electrode is preferably gold, silver or a composite material which consists of platinum or rhodium and a catalytic poison such as lead, sulfur, phosphorus, arsenic and their compounds formed by reaction with each other.

The invention will become more clear from the following detailed description taken with the accompanying drawings, in which:

FIG. 1 is a sectional view of an oxygen concentration cell having a non-catalytic metal electrode on an exhaust gas side according to the invention;

FIG. 2 is a similar view but showing employment of a composite material electrode;

FIG. 3 is a sectional view of an oxygen sensor according to the invention disposed in an exhaust duct;

FIG. 4 is a graph showing qualitatively concentrations of oxygen and carbon monoxide in an engine exhaust gas as functions of the A/F of an air-fuel mixture supplied to the engine; and FIG. 5 is a graph showing qualitatively the relationship between the A/F and the magnitude of EMF developed in the cells of FIGS. 1 and 2 and a conventional cell when the cells are exposed to the exhaust gas of FIG. 4.

Based upon considerations of the influence of a conventional concentration cell platinum electrode on oxidation reactions, the invention contemplates to employ a material having no catalytic action on oxidation reactions as a cell electrode to be exposed to a sample gas such as an engine exhaust gas. The material is required also to have good electric conductivity and a sufficiently high heat resistance.

According to the invention, an oxygen concentration cell 10 of FIG. 1 to serve as an oxygen sensor consists of a solid electrolyte layer 11, a first electrode 12 deposited on a side of the layer 11 to communicate with a reference gas and a second electrode 13 deposited on the opposite side of the layer 11. The general construction of the cell 10 is the same as conventional cells, and both the electrolyte layer 11 and the first electrode 12 are made of conventional materials. Examples of suitable solid oxygen-ion electrolytes are solid solutions of zirconia $ZrO_2$, ceria $CeO_2$ or thoria $ThO_2$ and a stabilizing oxide such as calcia CaO. Platinum is usually used as the first electrode 12 material. The second electrode 13 is made of gold or silver and is formed in a similar manner as the conventional platinum electrode 12 so as to be sufficiently gas permeable. For example, a paste containing gold or silver powder and an organic binder is applied on the surface of the layer 11 and is heated to remove the binder and to fix the metal powder to the electrolyte 11.

The electrode 13 made of gold or silver exhibits no catalytic action on oxidation reactions even at high temperatures, so that the EMF characteristic of the cell 10 is in good agreement with the Nernst's equation as is described hereinafter. It may be possible to select an alternative material for gold and silver from other non-catalytic metals and alloys of high melting point and electric conductivity.

Furthermore, the present invention provides another group of non-catalytic materials other than ordinary metals and alloys to form the electrode 13. Another cell 10A of FIG. 2 is fundamentally similar to the cell 10 of FIG. 1 except that a second electrode 13A thereof is made of a composite material consisting of a conventional electrode material such as platinum or rhodium and a substance which functions as a catalytic poison. Lead, sulfur, phosphorus, arsenic and their compounds formed by reaction with each other or with a halogen are preferred examples of the poisoning substances. The composite material electrode 13A can be formed similarly to the metal electrodes 11 and 13 using a paste containing a mixture of the metal and the poisoning substance powders in an organic binder. The cell 10A having thus formed electrode 13A shows an EMF characteristic approximately equal to that of the cell 10 of FIG. 1.

It is permissible to form the first electrode 12 with the same material as the second electrode 13 though is of no particular benefit.

FIG. 3 shows an oxygen sensor 14 as a preferred embodiment of the invention. A top-sealed tube 15 made of a solid solution of 85 mole% $ZrO_2$ and 15 mole% CaO serves as the oxygen-ion electrolyte layer 11 of FIG. 1. The first electrode 12 of platinum is deposited on the inner surface of the tube 14, and the second electrode 13 of gold is deposited on the upper portion including the sealed end of the outer surface of the tube 14. An attaching metal member 16 is fixed to the bottom side of the tube 14 establishing a good electrical connection with the exterior electrode 13, and a pair of platinum wire leads 17 connect the two electrodes 12 and 13 to a potentiometer 18.

The osygen sensor 14 is produced preferably by the following method. The inner and outer surfaces of the stabilized zirconia tube 15 are initially roughened by means of sand-blast. A paste containing platinum powder dispersed in an organic binder and another paste containing gold powder are applied on the inner surface and on the upper portion of the outer surface of the tube 15, respectively, and then the tube 15 is baked at 900°C for 1 hr. Both the resulting electrodes 12 and 13 are porous enough to allow the surfaces of the tube 15 to communicate with atmospheres surrounding the respective electrodes 12 and 13.

A second preferred embodiment of the invention is identical with the oxygen sensor 14 shown in FIG. 3 except for the material of the second electrode 13. In this embodiment, the second electrode 13 corresponds to the composite material electrode 13A of FIG. 2 and comprises platinum, lead and sulfur. The composite material electrode 13A is formed by applying a paste containing a 50/25/25 by weight mixture of finely powdered Pt, Pb and S dispersed in an organic binder followed by baking at 1,100°C for 1 hr. Alternatively, a paste containing finely powdered Pt and PbS may be used. The thus formed electrode 13A is porous like the above described gold electrode 13.

The oxygen sensors 14 according to the invention, one having the second electrode 13 of Au and another of Pt/Pb/S, and a conventional sensor of the identical construction but having a second electrode of Pt were subjected to an experiment to examine the EMF characteristic in an actual engine exhaust gas stream. A six-cylinder automobile engine of 2,000 cm³ displacement was used, and the test sensors 14 were disposed in an exhaust manifold 19 as seen in FIG. 3, so that the second electrodes 13 were exposed to an exhaust gas E. Air A was introduced into the interiors of the tubes 15 as a reference gas to communicate with the first electrodes 12. The engine was operated under the condition of the modified AMF ten-mode cycle. The concentrations of oxygen and carbon monoxide in the exhaust gas were measured analytically, and showed a progressive increase and decrease, respectively, as the A/F of the air-fuel mixture was increased as shown in FIG. 4. The point S represents the stoichiometric ratio of approximately 14.5.

The results of the experiment are shown by the graph of FIG. 5, in which the curves I, II and III represent the sensors having the second electrodes of Au, Pt/Pb/S and Pt, respectively. As is described hereinbefore, the curve III obtained using a conventional Pt electrode sensor shows an extreme deviation from a theoretical curve estimated from the concentration curves of FIG. 4 and the Nernst's equation. The abrupt transition of the EMF level at the point S means doubtless that oxidation reactions are caused to proceed to attain equilibrium during measurement. On the other hand, the curves I and II of the sensors having non-catalytic electrodes of the invention are almost identical with the CO concentration curve of FIG. 4 or bear inverse relationships with the $O_2$ concentration, well following the Nernst's equation.

These experimental results are considered sufficient to justify the assumption with respect to the catalytic action brought about by the Pt electrode and verify the advantages of the non-catalytic electrode materials according to the invention.

As is apparent from the above description, an oxygen sensor according to the invention can, due to close relationship between the EMF and oxygen concentration, detect both quantitatively and continuously the oxygen concentration in an exhaust gas and hence the concentration in a combustible mixture from which the exhaust gas is produced. Accordingly, employment of this oxygen sensor in a control system makes it possible to regulate precisely the A/F of an air-fuel mixture fed to an automobile engine to a predetermined value whether the value is near the stoichiometric ratio or is somewhat deviated from it.

What is claimed is:

1. In an oxygen sensor having a layer of a solid oxygen-ion electrolyte, a first electrode formed on one side of said layer to communicate with a reference gas and a second electrode formed on the opposite side of said layer to communicate with a gas subject to measurement of oxygen content, the improvement comprising said second electrode being made of a composite material comprising a platinum group metal selected from the group consisting of platinum and rhodium and at least one catalytic poison selected from the group consisting of lead, sulfur, phosphorous, arsenic and their compounds formed by reaction with each other, said catalytic poison amounting to such that said complex material is devoid of catalytic activity with respect to oxidation of carbon monoxide and hydrocarbons in an engine exhaust gas.

2. The improvement as claimed in claim 1, wherein said composite material contains substantially 50% by weight of Pt, 25% by weight of Pb and 25% by weight of S.

3. An oxygen sensor for measuring oxygen concentration in an engine exhaust gas, comprising a tubular body made of a solid solution of $ZrO_2$ and CaO, one end thereof being sealed, a first electrode of Pt deposited on the inner surface of said body and a second electrode deposited on the outer surface of said body including the sealed end, said second electrode being made of a material which is devoid of catalytic action with respect to oxidation of carbon monoxide and hydrocarbons, and said material containing substantially 50% by weight of Pt, 25% by weight of Pb and 25% by weight of S.

* * * * *